(12) United States Patent
Alexandrov et al.

(10) Patent No.: US 7,909,505 B2
(45) Date of Patent: Mar. 22, 2011

(54) METHOD AND DEVICE FOR INVESTIGATION OF PHASE TRANSFORMATIONS IN METALS AND ALLOYS

(75) Inventors: Boian Todorov Alexandrov, Upper Arlington, OH (US); John C. Lippold, Hilliard, OH (US); Seth Jason Norton, Katy, TX (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 12/349,196

(22) Filed: Jan. 6, 2009

(65) Prior Publication Data

US 2009/0119057 A1 May 7, 2009

Related U.S. Application Data

(62) Division of application No. 11/410,277, filed on Apr. 24, 2006, now Pat. No. 7,473,028.

(60) Provisional application No. 60/673,879, filed on Apr. 22, 2005.

(51) Int. Cl.
*G01N 25/02* (2006.01)
*G01K 3/08* (2006.01)
(52) U.S. Cl. ............... 374/10; 374/102; 374/1; 374/32; 374/16; 374/11; 374/12
(58) Field of Classification Search .......... 374/141, 374/29–39, 10–12, 14–16, 25–28, 43–45, 374/100–104, 160, 4–5, 1, 134, 129, 57, 374/139; 436/147; 422/51; 72/6.1, 11.3, 72/16.5, 19.1, 342.1, 342.6; 428/544; 29/615, 29/616, 617, 627, 50, 201; 148/121, 508, 148/511, DIG. 107
See application file for complete search history.

(56) References Cited

U.S. PATENT DOCUMENTS

| 3,100,253 | A | * | 8/1963 | O'Connor | 219/503 |
|---|---|---|---|---|---|
| 3,266,307 | A | * | 8/1966 | De Winter | 374/34 |
| 3,336,790 | A | * | 8/1967 | Nedumov | 374/11 |
| 3,456,490 | A | | 7/1969 | Stone | |
| 3,643,491 | A | * | 2/1972 | Dell et al. | 374/11 |
| 4,198,679 | A | * | 4/1980 | Fainzilberg | 702/136 |
| 4,248,083 | A | * | 2/1981 | Lacy et al. | 374/31 |
| 4,274,284 | A | * | 6/1981 | Hance | 374/139 |
| 4,443,118 | A | * | 4/1984 | Cure | 374/26 |
| 4,627,740 | A | * | 12/1986 | Jerde et al. | 374/1 |
| 4,781,469 | A | * | 11/1988 | Turon-Lagot | 374/27 |
| 4,854,724 | A | * | 8/1989 | Adams et al. | 374/5 |
| 4,901,061 | A | * | 2/1990 | Twerdochlib | 340/604 |

(Continued)

OTHER PUBLICATIONS

O.M. Akselsen, T. Simonsen, Techniques for examining transformation behaviour in weld metal and HAZ, Pergamon Journals Ltd., 1987, vol. 25, No. 1/2, pp. 26-34, Great Britain.

(Continued)

*Primary Examiner* — Gail Verbitsky
(74) *Attorney, Agent, or Firm* — Dinsmore & Shohl LLP

(57) ABSTRACT

A device and method for investigating phase transformation properties and structural changes of materials. In one form, the device simulates actual thermal processing conditions, while the method can be used in both simulations as well as in actual processing conditions. An analysis using at least one of the device and method is referred to as a single sensor differential thermal analysis, as it compares the temperature recorded in a measured specimen against a reference thermal history without requiring the derivation of the reference thermal history from measured reference temperatures.

11 Claims, 15 Drawing Sheets

U.S. PATENT DOCUMENTS

| | | | | |
|---|---|---|---|---|
| 5,033,320 | A | * | 7/1991 | Baerts ...................... 73/864.59 |
| 5,043,905 | A | * | 8/1991 | Louvo et al. ................. 700/147 |
| 5,098,196 | A | * | 3/1992 | O'Neill ........................ 374/11 |
| 5,100,111 | A | | 3/1992 | Thomas |
| 5,288,147 | A | * | 2/1994 | Schaefer et al. ............... 374/10 |
| 5,356,217 | A | * | 10/1994 | Sheffield ...................... 374/45 |
| 5,762,768 | A | * | 6/1998 | Goy et al. ................ 204/298.13 |
| 5,788,373 | A | | 8/1998 | Huetter et al. |
| 5,876,118 | A | | 3/1999 | Vogel |
| 5,958,154 | A | * | 9/1999 | O'Handley et al. ........... 148/312 |
| 6,146,013 | A | * | 11/2000 | Huetter et al. ................. 374/46 |
| 6,318,890 | B1 | * | 11/2001 | Hutter et al. .................... 374/10 |
| 6,536,944 | B1 | * | 3/2003 | Archibald et al. .............. 506/12 |
| 6,796,144 | B2 | * | 9/2004 | Shepard et al. ............. 65/29.11 |
| 6,907,761 | B2 | * | 6/2005 | Spence et al. .................... 72/60 |
| 7,040,804 | B2 | * | 5/2006 | Inatomi et al. ................. 374/43 |
| 7,645,070 | B2 | * | 1/2010 | Atwood et al. ............... 374/137 |
| 2008/0112457 | A1 | * | 5/2008 | Mores ............................ 374/31 |
| 2009/0052494 | A1 | * | 2/2009 | Wijffels .......................... 374/10 |
| 2010/0021761 | A1 | * | 1/2010 | Ayer et al. .................... 428/660 |

OTHER PUBLICATIONS

D.G. Tecco, Determining continuous cooling transformation data for HAZs, Metal Construction, Jun. 1984, pp. 361-362, USA.

O.I. Steclov, N.G. Dariavash, O.A. Magnitsky, A.N. Hakimov, Automation of Tests Into Phase-Structural Transformation of Steels During Welding Using Micro-Computer, pp. 1-9, Doc. IX-1542-88.

R.H. Phillip, "In Situ" Determination of Transformation Temperatures in the Weld Heat-Affected Zone, 7 pages, Victoria, Australia.

Ernest F. Nippes, Warren F. Savage, Development of Specimen Simulating Weld Heat-Affected Zones, Welding Research Supplement, Nov. 1949, pp. 534-s-546-s, Troy, New York.

E.L. Makarov, D.B. Slinko, Dependence of austenite transformation temperatures of the weld metal on welding conditions, Weld Production, Feb. 1984, pp. 3-7, Svar. Proiz, 1984, No. 2, pp. 3-6.

A.N. Khakimov, N.G. Dar'Yavash, O.A. Maegnitskii, Application of microcomputers in thermal analysis in welding, Welding Production Aug. 1986, Svar. Proiz, 1986, No. 8, pp. 22-23.

Henri Granjon, The 'implants' method for studying the weldability of high strength steels, Welding Journal, Nov. 1959, pp. 509-515.

D. Farson, R. Richardson, X. Li, Infrared Measurement of Base Metal Temperature in Gas Tungsten Arc Welding, Welding Research Supplement, Sep. 1998, pp. 396-s-401-s, USA.

Kenneth Easterling, Introduction to the Physical Metallurgy of Welding, Butterworths Monographs in Metals, pp. 23-33, University of Lulea, Sweden.

* cited by examiner

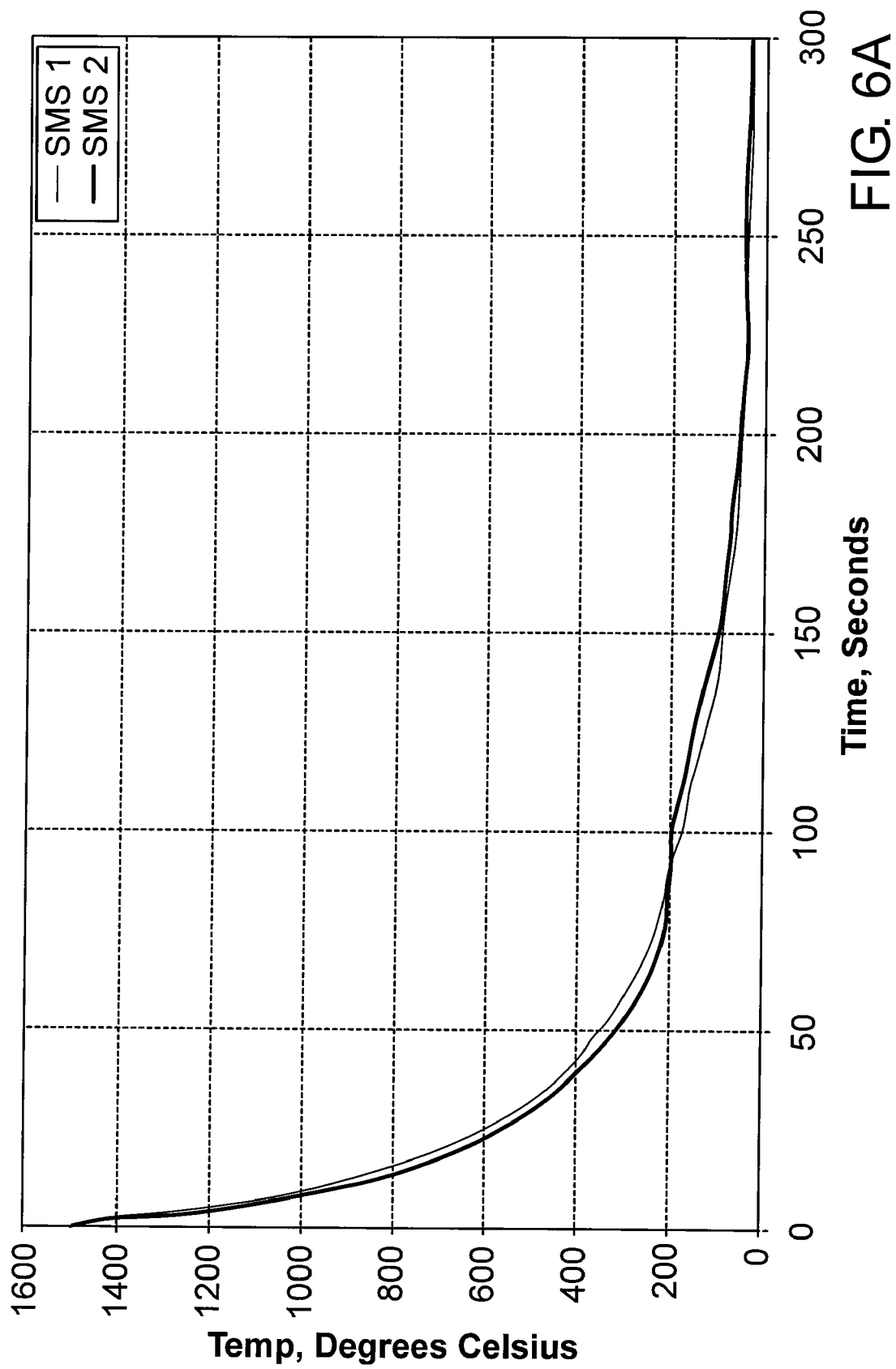

METHOD AND DEVICE FOR INVESTIGATION OF PHASE TRANSFORMATIONS IN METALS AND ALLOYS

CROSS-REFERENCE TO RELATED APPLICATION

This application is a divisional of (and now-allowed) application Ser. No. 11/410,277, filed Apr. 24, 2006 now U.S. Pat. No. 7,473,028. This application claims the benefit of the filing date of U.S. Provisional Application No. 60/673,879, filed Apr. 22, 2005.

STATEMENT REGARDING FEDERALLY SPONSORED RESEARCH OR DEVELOPMENT

This invention was supported by the government under Contract No. DGE-0312160 awarded by the National Science Foundation (NSF). The government has certain rights in the invention.

BACKGROUND OF THE INVENTION

The present invention generally relates to a device and method for measuring the physical property of a material as a function of that material's temperature, and more particularly to a device and method for measurement of solid-liquid and solid-state phase transformations and structural changes in materials under simulated and actual conditions associated with thermal and thermo-mechanical processing of such materials.

The solid-liquid and solid-state phase transformation and structural changes that occur in metallic materials during thermal and thermo-mechanical processing determine their final microstructure and hence their mechanical and physical (in-service) properties. These phase transformations and structural changes are also closely related to the fabricability (weldability, castability, formability or the like) of conventional and modern structural alloys, and consequently to their successful implementation as materials for advanced structural applications.

Extensive investigations have been performed worldwide, aimed at developing practical methods to measure and subsequently control the phase transformations and structural changes in metallic materials, in order to improve their fabricability and structural properties. Effective methods for studying of phase transformations and structural changes can be used for the development of new materials and advanced processing applications.

There are known various techniques and devices for evaluating phase transformation information in simulated and actual material processing environments. Examples of such evaluation include thermal, differential thermal and dilatometric analyses.

The method for thermal analysis (TA) allows direct determination of phase transformation temperatures from heating/cooling curves where large thermal effects cause significant change of the heating/cooling rate. This method is mainly applicable in equilibrium conditions and can be used in simulated, as well as in-situ, conditions. TA can also be applied during processing when the phase transformations are accompanied by release of large amounts of heat as in solidification of castings, or large weld pools. TA is insensitive to phase transformations and structural changes with small thermal effects that occur at non-equilibrium heating and cooling rates, as for example in welding.

Differential thermal analysis (DTA), is used for investigating phase transformations in materials where a specimen of the investigated material and a reference specimen experience the same heating and cooling thermal cycle in a controlled environment. In such technique, the material of the reference specimen does not undergo any phase changes in the investigated temperature range, while that of the specimen being investigated typically does. The heat consumption or release that accompany the phase transformations impact the heating and cooling rates of the investigated specimen. These heat effects are revealed by plotting the difference in the temperature of the two specimens versus time or the current temperature. Changes in the sample that lead to release or absorption of heat can be used in determining the phase transformation temperatures of the sample. The method and devices for DTA have high sensitivity to the thermal effects of phase transformations and structural changes. The traditional DTA technique utilizes sophisticated and expensive devices that operate in a short range of heating and cooling rates of up to about twenty degrees Celsius per minute. Such limitation makes this approach inapplicable for investigating the phase transformation in materials where actual processing conditions must be simulated. For example, the heating and the cooling rates of actual processing conditions are normally much higher, reaching up to several hundred degrees per second.

Continuous cooling transformation (CCT) diagrams are one of two main types of transformation diagrams that are used to optimize a metal's processing path to achieve a given set of properties. CCT diagrams measure the extent of phase transformation as a function of time for a continuously decreasing temperature. This allows the metal to be heated and then cooled at some rate so that the degree of transformation can be measured by dilatometry or other methods. In welding (for example) these diagrams allow the welding engineer to select the range of cooling rates, and the respective operational window of heat inputs that provides the optimal combination of microstructural constituents in the heat affected zone (HAZ) and weld metal. CCT diagrams are typically constructed by simulating weld thermal histories over numerous laboratory scale specimens. This approach is limited in depicting the actual heating and cooling rates and thermal gradients, and utilizes expensive, specialized equipment. Such an approach is not applicable for investigating solidification and solid-state phase transformations in the weld metal and therefore is not useful for constructing weld metal CCT diagrams. DTA methods and devices were also used for constructing CCT diagrams; however, because of the maximum heating and cooling rates for these techniques are so low, they are generally inappropriate for constructing a useful CCT diagram.

Methods for investigating the phase transformations under actual welding conditions have been conducted, where the temperature changes in a particular point of a real welded joint during welding were recorded. The method of differentiation of recorded thermal histories can be applied in-situ by analog or digital differentiation of the weld thermal history, in order to reveal the small thermal effects of phase transformations occurring in the HAZ. Disadvantages of such a method include the amplification of electromagnetic noise, recorded over the thermal cycle, the low sensitivity to and difficult recognition of higher temperature phase transformations, and low accuracy of determining phase transformation starting and finishing temperatures.

More recently, the original two-thermocouple version of DTA was applied during actual welding and partly solved some of the above mentioned problems. In such approach the reference thermal cycle is recorded by a thermocouple inserted into a tube of austenitic stainless steel, which does not undergo solid-state phase changes. The two thermocouples are equally positioned into the heat affected zone (HAZ) of the investigated carbon steel. The measured and the reference thermal histories, and the temperature difference between them are recorded. The sensitivity to heat effects of phase transformations in this approach depends on the distance between the two thermocouples, and further needs repetitive experiments to be optimized. In addition, the experiment is difficult to control. The manner of obtaining the reference thermal cycle limits the applicability of this approach only to solid-state phase transformations in the HAZ and does not allow investigating the solidification behavior and the other phase transformations in weld metal.

Dilatometric analysis (DA) is based on measuring the volume changes that accompany the phase transformations in metallic materials. This method is mainly applied in combination with devices for simulation of thermal and thermomechanical processing, and is capable of determining the solid-state phase transformations only. Since DA has low sensitivity to some solid-state phase transformations, it is inapplicable for solid-liquid phase transformations, and is insensitive to most structural changes. Dilatometry can be used to evaluate actual thermal cycles and heating and cooling rates associated with those cycles in such a way as to quantify dimensional changes of the material produced by such changes in temperature. Nevertheless, DA cannot be used in-situ, as it requires special sample types and can only detect phase transformations where there is a significant change in sample dimension. In addition, it cannot detect structural changes, such as recrystallization.

Different devices for simulation of thermal and thermomechanical processing are available. Such devices are based on resistance, induction, convection or light radiation heating of laboratory scale specimens. These devices use dilatometric analysis for determining the solid-state phase transformation temperatures. Because of the control loops used for controlling the heating and cooling rates, DTA is inapplicable in combination with such devices. Some thermo-mechanical simulators are not capable of reproducing the extremely high heating and cooling rates at the high temperature range that are typical for the most welding processes. This results in longer dwell times in austenite phase field (for steels), leading to larger grain size, lower transformation temperatures and consequently higher content of lower temperature products of austenite decompositions and higher hardness in the simulation specimens, compared to the real HAZ. The above technique is not capable of simulating the solid-liquid and solid-state phase transformations. In addition, the simulation equipment is complex in shape and involves expensive laboratory setups.

In another form, weld microstructure simulation equipment based on light radiation heating has been disclosed. The specimen is heated by focused high-power lamps and the specimen's temperature is controlled by a thermocouple. The cooling rate is controlled by the flow rate of a stream of shielding gas and simultaneous heating. The HAZ simulation specimen is a small thin wall tube that is in continuous contact with a dilatometer that is used to determine the phase transformation temperatures. The weld simulation specimen is a small cylinder that is attached to a thermocouple and melts over it forming a small ball. The solidification temperature range is determined by differentiation of the thermal history (measured by the thermocouple) using an analog electronic device. The main disadvantages of this equipment are that it has difficulty in resembling the actual weld and HAZ heating and cooling rates. In addition, it exhibits non-uniform heating of the HAZ simulation specimen. Moreover, the small volume of the weld simulation specimen does not allow resembling the actual weld solidification patterns.

The available methods and devices have a number of disadvantages that limit their usefulness for measuring phase transformations and structural changes in structural alloys during actual or simulated processing. Thus, what is desired is a method for determining phase transformation temperatures and structural changes under either simulated or actual operating environments for material processing. What is also desired is a device for performing more accurate simulations to evaluate material phase transformations and structural changes.

SUMMARY OF THE INVENTION

These desires are met by the present invention, where a device is configured for measuring simulated temperatures that are associated with actual material processing conditions, and converting such measured temperatures into phase transformation or structural change information. The method of the present invention includes a technique for identifying phase transformations and structural changes in metals and alloys under either simulated or actual metal processing conditions. From measured temperature values, a thermal history of the metal specimen being processed or evaluated is recorded for the regimes that undergo phase transformations. From this thermal history, the phase transformation temperatures can be determined by what the present inventors refer to as single sensor differential thermal analysis (SSDTA), which differs from conventional DTA in that rather than relying on the acquisition of actual reference temperature data with which to compare sensed specimen temperature, the reference temperature is calculated using numerical modeling or a related algorithm based on temperature measured by the single sensor. SSDTA does not mean that only a single temperature measurement sensor be present (as multiple sensors can be used in different locations within the same specimen (corresponding, for example, to the areas of solid, liquid or a solid-liquid state)), but merely that the device and method does not require the presence of a reference sensor with which to compare measured temperature values against in order to establish phase transformation or related structural change information.

The capability of the SSDTA method is valuable for numerous actual and simulated metal processing applications. In welding-specific examples, it can be used for investigating the solidification range and solid-state phase transformations under actual welding conditions, constructing CCT diagrams for as-solidified and heat-affected weld metal. For example, valuable information is provided about the weld metal microstructure evolution in the typical range of cooling rates for shielded metal arc welding (SMAW). The range of welding conditions which provide an optimal combination of microconstituents with respect to weldability and mechanical properties is determined. The SSDTA method provides reliable, fast and inexpensive monitoring of phase transformations under actual welding conditions. This can be beneficial for the development of welding consumables and welding procedures. Of course, the benefits are not limited to welding, and it will be appreciated by those skilled in the art that other material processing applications can be used. For example, the SSDTA can also be used for determining forging and heat treatment temperatures ranges, the onset of recrystallization, and ferromagnetic/paramagnetic transformations (the Curie temperature), among other things.

The present invention can be useful in correlating the solidification ranges of material specimens and their solidification cracking temperature ranges (SCTRs). The SSDTA method has great potential for determining weld solidification cracking susceptibility based on the actual solidification temperature range. It allows the detection of eutectic phase formation and the determination of such material-specific parameters as the size of the solidification range and the non-equilibrium liquidus and solidus temperatures that are directly related to solidification cracking susceptibility. Compared to conventional DTA, the SSDTA has equal or similar accuracy, and is further applicable in actual processing, as well as in simulation of non-equilibrium processing conditions.

Compared to the methods for revealing the thermal effects of phase transformations over the recorded thermal history (thermal analysis) and the methods for analog and digital differentiation, the proposed SSDTA method allows more precise determination of the phase transformation start and finish temperatures. In addition, compared to the in-situ application of the two thermocouple DTA method, the new technique does not use a reference thermocouple or related sensor, thus simplifying the measurement and allowing its application in weld metal and avoiding additional experiments for determining the optimal distance between the thermocouples in order to optimize the sensitivity. Moreover, it permits controlling the sensitivity to the thermal effects of phase transformations and processing separate parts of the measured thermal histories, thus increasing the accuracy. Thus, it can be seen that the SSDTA method has tremendous application potential for the reliable determination of the solid-liquid and solid-state phase transformation temperatures and structure changes under the conditions of actual or simulated welding, casting, heat treatment and other thermal and thermo-mechanical processes.

The SSDTA method is verified by comparison to dilatometric analysis using a commercially-available thermal simulator. The SSDTA method is also verified by comparison to conventional DTA using commercially-available DTA equipment. The accuracy of the SSDTA method is confirmed by determining the solidification temperature and the Curie temperature in pure metals. The results of these tests proved that SSDTA has higher sensitivity to phase transformations than dilatometric analysis. It was also shown that SSDTA has equal sensitivity and accuracy with the conventional DTA in determining phase transformations and structural changes. The SSTDA is applicable in actual and simulated processing conditions, thus providing a superior alternative to the available in-situ and simulation techniques that generally use different variations of DTA or dilatometric analysis for determining the phase transformation temperatures.

According to a first aspect of the invention, a method of conducting single sensor differential thermal analysis of a material is disclosed. The method includes placing a specimen of the material in thermal communication with a heat source, heating the specimen with the heat source, acquiring data associated with measuring a temperature of the specimen, calculating reference data, comparing the acquired and reference data, and generating phase transformation temperatures based on the computed temperature differences. In the present context, calculating reference data may include retrieving the data from a storage location, such as a computer memory, lookup table or the like.

Optionally, the method can be part of a larger metal processing application, examples of which include welding, surfacing, hardfacing, brazing, soldering, thermal cutting, casting, heat treatment, forging, rolling, extruding, surface melting and other thermal or thermo-mechanical processing. The method may be for a real processing step in an actual metal processing environment, or may be a simulation of non-equilibrium solid-liquid and solid-state phase transformations. In the present context, a phase transformation is considered to be non-equilibrium if it does not strictly obey the material's phase diagram which is determined under conditions of thermal and chemical equilibrium. The method may further include reducing exposure of the temperature measuring sensor to electromagnetic noise during the temperature measuring. In one form, reducing exposure can be achieved by grounding one or more of a data acquisition system and a temperature measuring sensor. In another option, the calculated reference data can be generated by a known formula, where the temperature information can be derived exclusively from the temperature data taken from the specimen. In yet another option, the power output of a simulation device can be controlled to closely follow a predetermined thermal history through a feedback-based control loop. In addition, the method can include compensation in heating and cooling rates caused by the thermal effects of phase transformations and structural changes. In this way, a predetermined thermal history, while simultaneously recording the power output of the simulation device, can be realized.

According to another aspect of the invention, a device for investigating phase transformations in a material is disclosed. The device includes a chamber defining a substantially enclosed environment, a source of energy configured to heat a specimen of the material that is placed in the chamber, and a mold defining a place where the specimen can be either placed while being heated, or where the specimen can be collected in once it has been partially or completely melted. In the present context, the term "substantially" refers to an arrangement of elements or features that, while in theory would be expected to exhibit exact correspondence or behavior, may, in practice embody something slightly less than exact. As such, the term denotes the degree by which a quantitative value, measurement or other related representation may vary from a stated reference without resulting in a change in the basic function of the subject matter at issue. In addition, the device includes a hearth that is either disposed in the chamber or forms a part (such as a lower surface) thereof. The hearth is configured to be cooperative with the mold such that upon heating of the specimen in the chamber, at least a molten portion of the specimen collects in the mold. In addition, the device includes a data acquisition system that includes a temperature measuring sensor and a computation device. The temperature measuring sensor is placed adjacent the specimen such that it is in thermal communication therewith to sense the temperature of the specimen, while the computation device (for example, a computer) converts the measured temperature data into phase transformation information. Conversion of the measured temperature data is facilitated by comparing it to reference thermal data such that differential data that corresponds to specimen phase transformation is produced.

According to yet another aspect of the invention, a device for investigating phase transformations in a metallic specimen under simulated operating conditions is disclosed. The device includes a chamber and a source of energy configured to heat the metallic specimen, both as described in conjunction with the previous aspect. In addition, the device includes a mold that collects a molten portion of the metallic specimen therein upon heating of the specimen. The device also includes a hearth disposed in or forming a part of the chamber. Passages formed in the hearth can be used for controlled atmosphere conduit. The device further includes one or more temperature measuring sensors disposed relative to the specimen to sense its temperature.

BRIEF DESCRIPTION OF THE SEVERAL VIEWS OF THE DRAWINGS

The following detailed description of the preferred embodiments of the present invention can be best understood when read in conjunction with the following drawings, where like structure is indicated with like reference numerals and in which:

FIG. 6A illustrates two measured cooling histories generated during a specimen processing simulation;

DETAILED DESCRIPTION OF THE PREFERRED EMBODIMENTS

Figure 1:
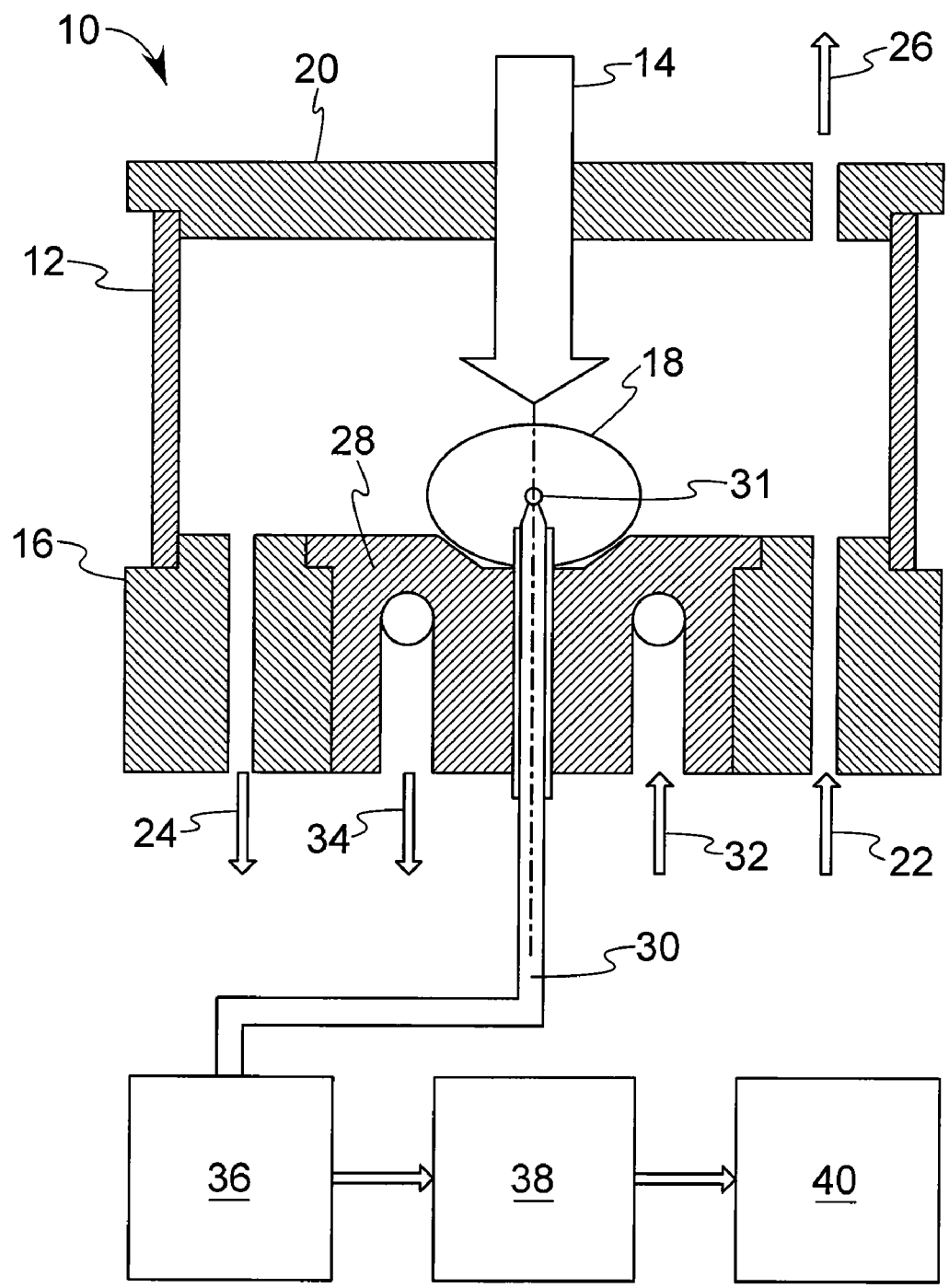
FIG. 1 illustrates a cutaway view of a device for investigating phase transformations according to an embodiment of the present invention.
Figure 2:
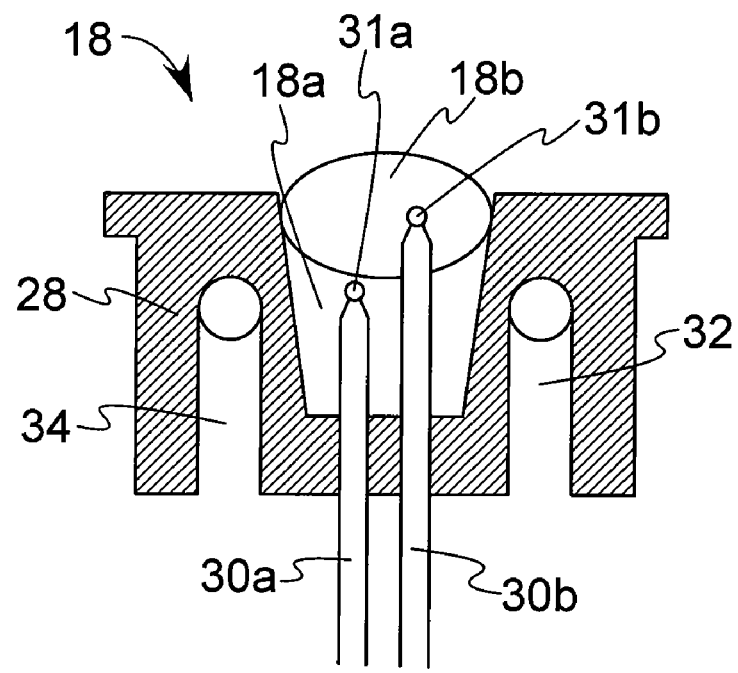
FIG. 2 illustrates a cutaway view of a first mold configuration.
Figure 3:
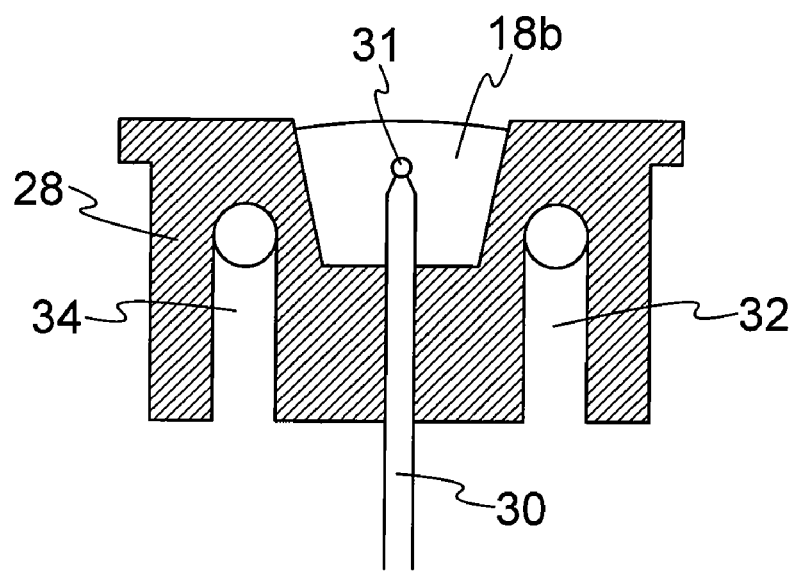
FIG. 3 illustrates a cutaway view of a first mold configuration where a single temperature-measuring device is being used.

Referring first to FIGS. 1 through 3, an embodiment of the device 10 according to the present invention includes a chamber 12, a source of energy 14, and a hearth 16 (shown with particularity as 16A) on which a specimen of material 18 is heated. Specimens 18 can exist in a solid state (i.e., not melted), solid-liquid state (i.e., partially melted) or liquid state (i.e., completely melted). The chamber 12 is made of a heat-resistant material (such as metals and their alloys), and forms a hermetic seal between the hearth 16 and a lid 20. In certain forms, the heat-resistant chamber material may be transparent, such as the aforementioned borosilicate glass. In one form, the chamber 12 forms a hermetic seal between the hearth 16 and lid 20. A controlled atmosphere is maintained in the chamber 12 to protect the specimen 18 from the surroundings, and may include an inlet 22 and outlet 24. In addition, a vacuum 26 can be used to help maintain the controlled atmosphere. The specimen 18 weight and shape depending on the application. The source of energy 14 may be in one or more numerous forms, and either concentrated or non-concentrated. Examples of the first include an electric arc or plasma arc, plasma, laser or electron beam, while examples of the second include induction heating, convection heating or the like. In the version shown, the source of energy 14 enters the chamber 12 through the lid 20 and heats the specimen 18, although it will be appreciated by those skilled in the art that the precise location of the source of energy 14 relative to the chamber 12 is not critical.

The hearth 16 is made of a high thermal conductivity or heat resistant material, and may be configured in one of at least two configurations, both of which may include a mold 28. The first configuration hearth 16A, as shown in FIGS. 1 through 3, utilizes one or more replaceable molds 28 (shown with particularity as mold 28A) that hold the specimen 18 and facilitate its heating. The mold 28 is cooled by internal liquid cooling passages, with one or more cooling liquid inlet passages 32 and one or more cooling liquid outlet passages 34.

Figure 4:
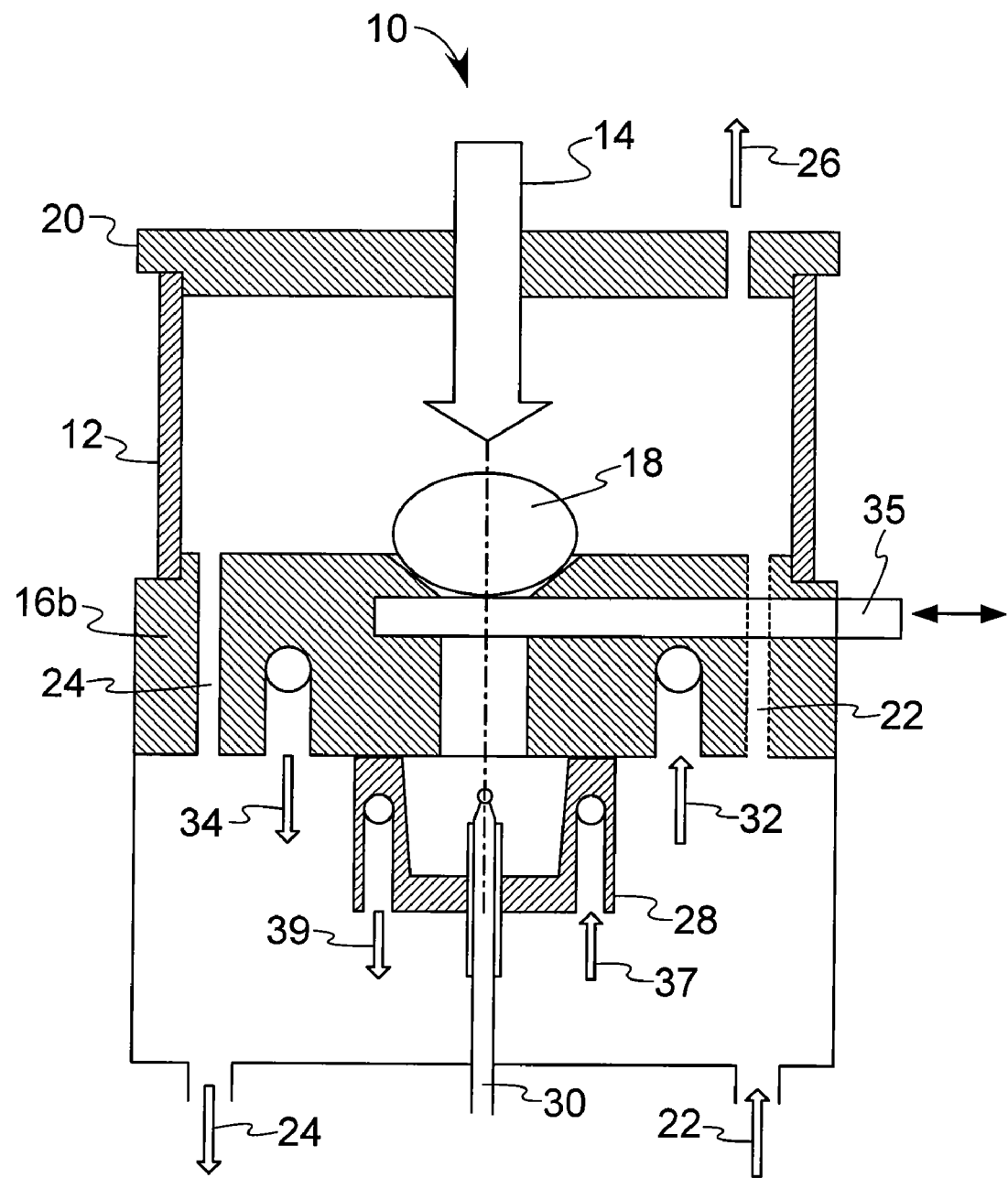
FIG. 4 illustrates a cutaway view of an alternate embodiment of the present invention.

In the second configuration, as shown in FIG. 4, hearth 16B is intended for complete melting of the specimen 18. Hearth 16B is equipped with a transfer mechanism 35 by which the molten material 18 is cast into a replaceable mold 28B, positioned below the hearth, FIG. 4. The transfer mechanism 35 separates the hearth 16 from the mold 28 in order to melt the specimen 18 completely in the hearth 16. After the specimen 18 is completely melted, the transfer mechanism 35 is opened, thus allowing the molten metal to flow down into the mold 28. The transfer mechanism 35, an example of which can be a gate valve, is disposed between the hearth 16B and the mold 28B to allow transfer of molten metal from the hearth 16B to the mold 28B. In a variation, the molten metal from specimen 18 in the hearth 16 is delivered through open hearth with a central hole. The specimen 18 is melted over the hole and the molten metal passes through it and enters the mold 28. The molds 28 for both hearth designs are made of heat resistant or refractory material and may be internally liquid cooled as previously discussed. For example, the molds 28A, 28B can be made from a ceramic, a bimetallic or a metal coated with a ceramic or related refractory. After melting, the specimen 18 is transferred into a mold 28B where it solidifies. The hearth 16B simulates the conditions of casting and allows the liquid-solid and solid-state phase transformations to be determined during cooling, and to perform some weldability or castability tests.

The heating and cooling rates of the specimen 18 are controlled by simultaneously controlling the power regime of energy source 14 and the respective mold cooling capacity. The latter is controlled by the cooling liquid flow rate that passes through the cooling liquid inlet and outlet 32, 34, as well as the mold material thermal conductivity and capacity, and the mold mass and geometry. The high power density and large span of cooling capacity of device 10 allow simulation of a wide range of heating and cooling rates, as well as thermal gradients. Thus the device 10 is capable of reproducing the thermal conditions of variety of liquid-solid and solid-state metal processing applications including welding, surfacing, hardfacing, surface melting, casting, heat treating or the like. In addition, device 10 is capable of simulating some fabricability tests (for example, weldability tests, castability tests or the like), or some other idealized conditions.

This hearth 16A shown in FIGS. 1 through 3 can be used to simulate the conditions of welding, surfacing and surface melting. In the configuration shown in FIG. 1, the specimen 18 is heated by an electric arc in inert atmosphere; in-situations where the specimen 18 is melted, the material of the specimen 18 solidifies over thermocouple 30. Such a configuration allows investigation of the liquid-solid and solid-state phase transformations during cooling of the material of specimen 18. Referring with particularity to FIG. 2, the thermocouples 30 are capacitor discharge welded in holes in mold 28A so that the tips 31 would coincide respectively with the molten region 18B and HAZ 18A of specimen 18. This option allows investigating the liquid-solid and solid-state phase transformations during both heating and cooling. Referring with particularity to FIG. 3, the specimen 18 is melted by energy source 14 and solidifies in a ceramic mold 28A. The use of the ceramic mold 28A, with its relatively low thermal conductivity, allows investigating the liquid-solid and solid-state phase transformations at slow cooling rates.

A microprocessor-based system with an intelligent feedback loop can be used to control the energy source 14 power output regime in order to realize a predetermined thermal history at a particular mold 28 cooling capacity. The intelligent feedback loop includes continuous measuring the temperature of specimen 18, comparing it to the predetermined thermal history that may be stored in memory of computation system 38, adjusting the real time energy source 14 power output in order for the specimen 18 to follow the predetermined thermal history, and recording the regime of change of the power controlling parameters.

Existing thermal and thermo-mechanical simulation devices use a control loop to simulate predetermined thermal histories. This consists of continuous measurement of the temperature of the processed sample and comparing it to a predetermined thermal history. Their control loops are sensitive enough to compensate (such as by modification of the power output) for any deviations of the simulated thermal history from the predetermined one. They can also compensate the changes in the heating and cooling rate caused by the thermal effects of phase transformations and structural changes, thus making their use for thermal and differential thermal analyses inapplicable for measuring phase transformation temperatures and structural changes, and allowing only the less sensitive dilatometric analysis to be applied.

Figure 10:
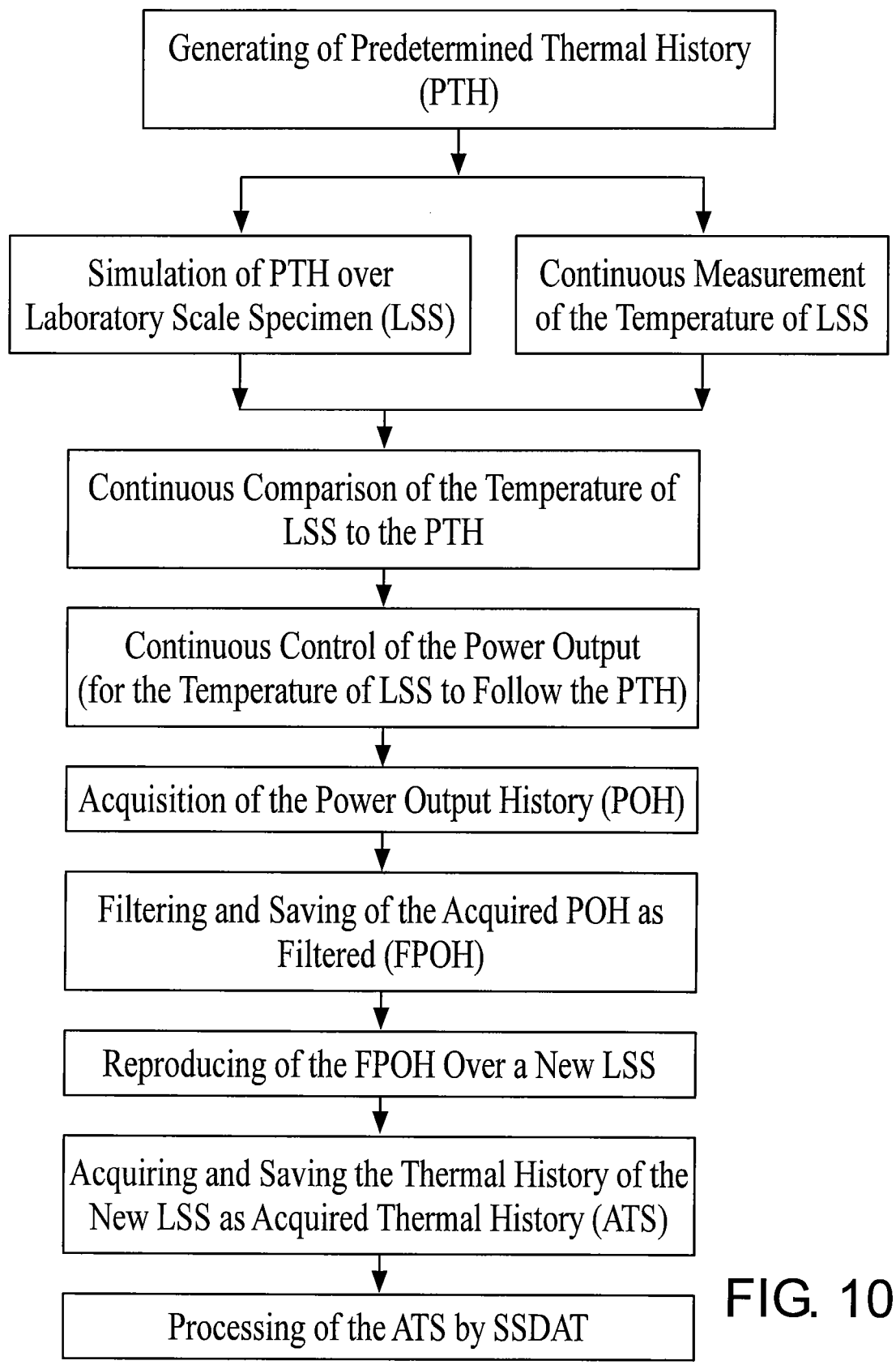
FIG. 10 illustrates a flow chart associated with an intelligent feedback loop according to the present invention.

Referring next to FIG. 10, a flow chart showing the application of the intelligent feedback loop to the present invention is shown, where the recorded power output parameters are filtered from any unwanted noise and from the effects of compensating the phase transformation heat effects. After that, the filtered power output is applied to reproduce the predetermined thermal history on a new specimen 18 of the same shape, size and material as the first one, without using a control loop. In this way, the intelligent feedback loop allows reproducing predetermined thermal histories without the device 10 compensating (erasing) the thermal effects of phase transformations and structural changes. This way, the SSDTA can be used for determining the phase transformation temperatures and structural changes with the simulation device 10. This approach also allows replacing or paralleling the standard dilatometric technique in available simulation devices for measuring phase transformations by the present SSDTA. Stated another way, instead of erasing the thermal effects of phase transformations (as is done in existing simulation devices), the intelligent feedback loop does not erase the phase changes, thus allowing the SSDTA to be used with the present and existing simulation devices.

Referring with particularity to FIG. 10, steps associated with using an intelligent feedback loop according to an aspect of the present invention is shown. First, a predetermined thermal history is generated. From there, a simulation of that thermal history and continuous measurement of the temperature of a laboratory scale specimen 18 are conducted, after which continuous comparisons are made between the measured temperature of specimen 18 and the thermal history. Results of this can be used to provide continuous control of the power output of the source of energy 14, thereby ensuring that the measured temperature in specimen 18 follows the predetermined thermal history. The computation system 38 (which as mentioned before may be a part of or cooperative with, data acquisition system 36) may be used to acquire, filter and save what is referred to as a power output history. The intelligent feedback loop can then reproduce the filtered power history over a new specimen 18. The computation system 38 can further acquire and save a thermal history associated with the new specimen 18 as an acquired thermal history, which can be processed by SSDTA.

The specimen temperature is measured by sensors 30 that can be contact or non-contact. These sensors 30 can be chosen from a variety of devices, such as thermocouples, infrared pyrometers, optical fiber sensors or other contact or non-contact sensors. The signals from the sensors 30 are recorded by a data acquisition system 36 and microprocessor-based computation system 38 (such as a personal computer) as thermal histories. The latter are then processed by SSDTA software 40 that is loaded in computation system 38 (in the form of a computer, calculator or other data-manipulating means) in order to reveal information related to the material, including phase transformation thermal effects and transformation start and finish temperatures. Although shown as three separate components in FIG. 1, it will be appreciated by those skilled in the relevant art that data acquisition system 36, computation system 38 and SSDTA software 40 may be integrated into a single unit 100, and that either configuration is equally applicable to the present invention. Furthermore, the temperature measuring sensors 30 may also form an integral part of the data acquisition system 36.

Figure 5A:
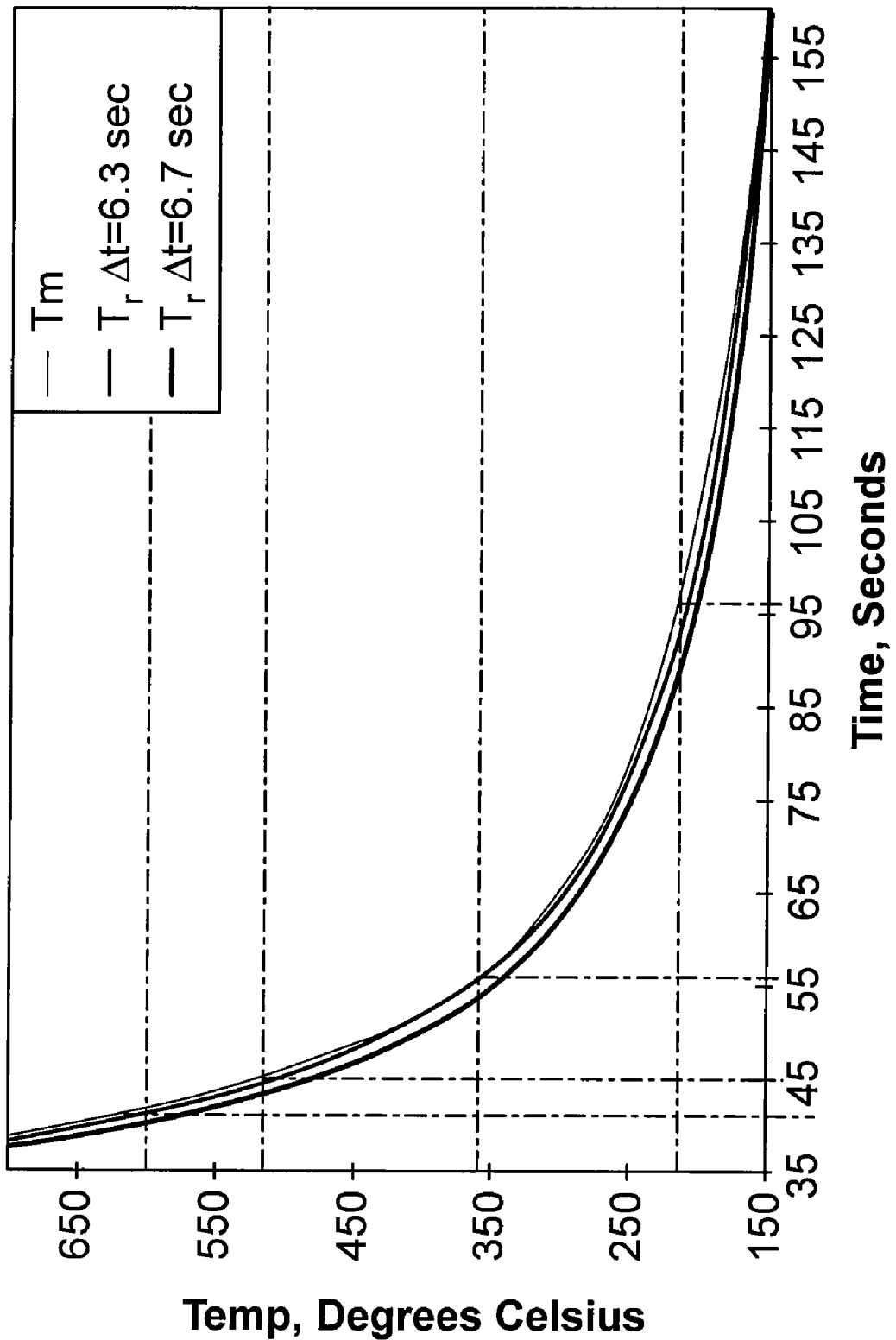
FIG. 5A represents the measured cooling thermal history and two reference curves of high strength low alloy steel according to an aspect of the present invention, where the reference curves are generated by optimizing only the time parameter.
Figure 5B:
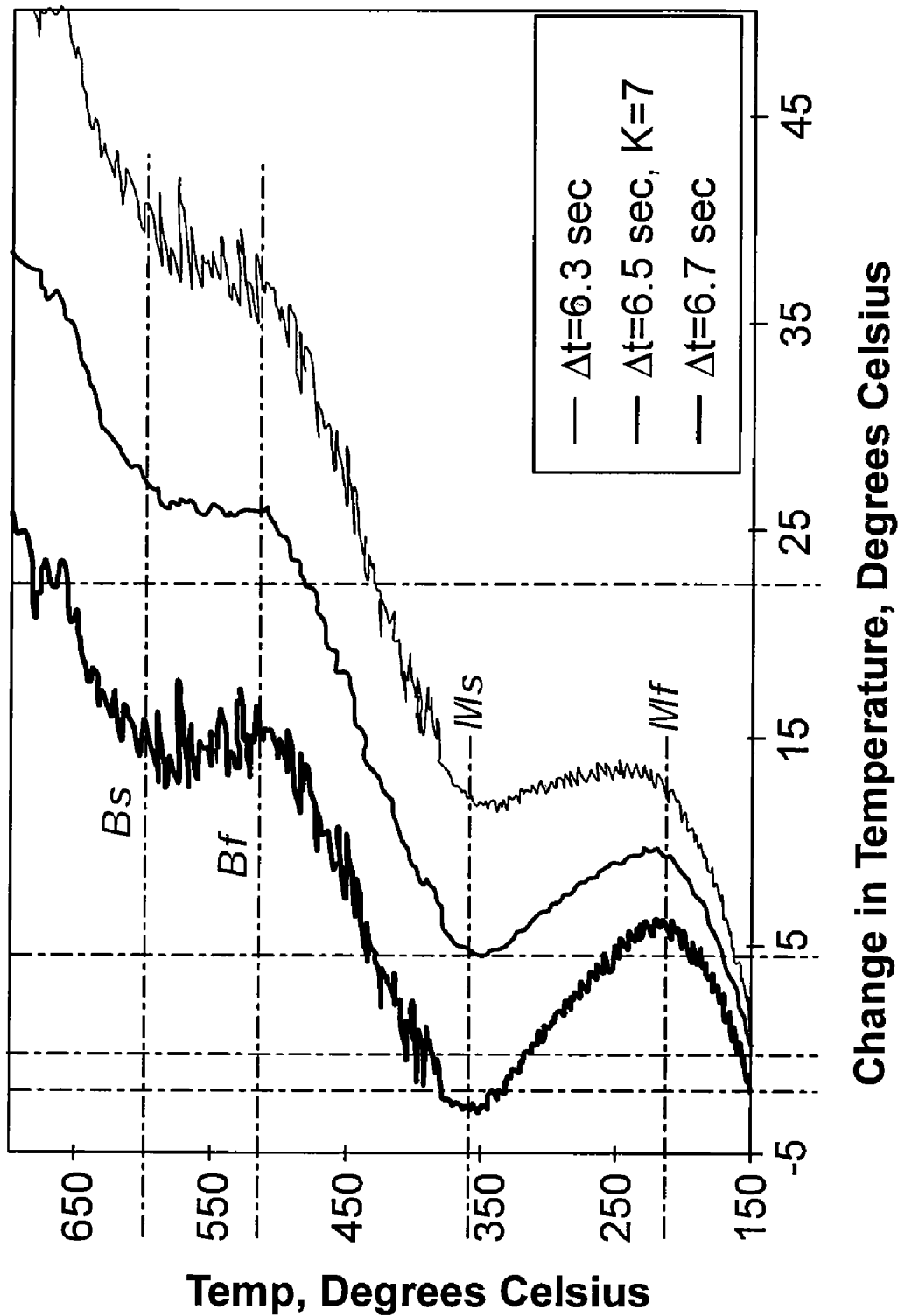
FIG. 5B represents increased sensitivity in determining the phase transformation heat effects due to the generated reference curve of FIG. 5A, where temperature change is presented as a function of the temperature.
Figure 5C:
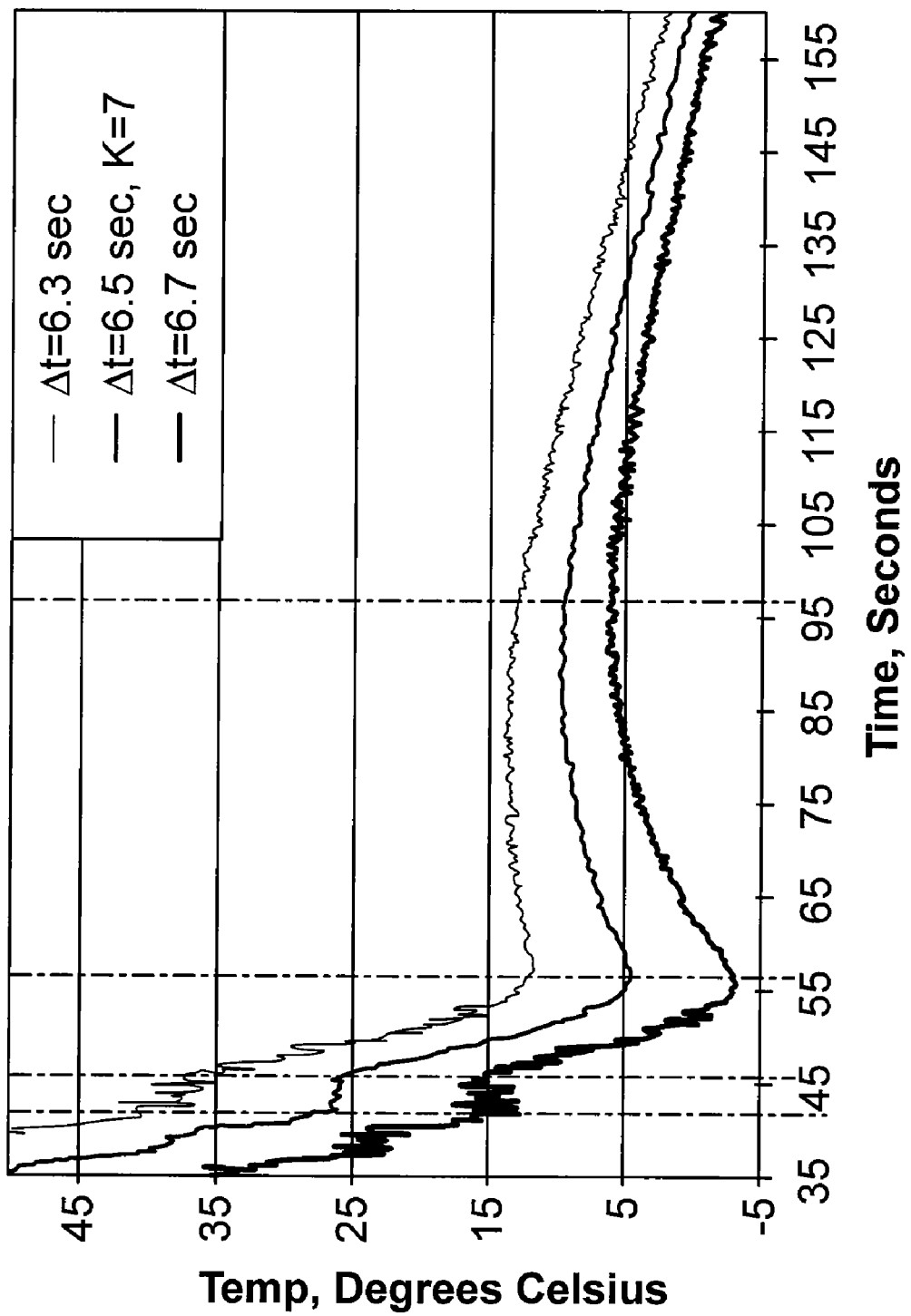
FIG. 5C represents increased sensitivity in determining the phase transformation heat effects due to the generated reference curve of FIG. 5A; where temperature change is presented as a function of time.

FIGS. 5A through 5C show an example of SSDTA according to an aspect of the present invention. Referring first to FIG. 5A, the measured cooling thermal history (Tm) and two reference curves (Tr) at two different times, 6.3 and 6.7 seconds are shown. These reference curves are generated by optimizing only the parameter $\Delta t$ in the analytical formula discussed below. Generating a reference curve that is closer to the measured thermal history increases the sensitivity in determining the phase transformations heat effects. This can be seen in FIGS. 5B and 5C, where by reducing the $\Delta t$, which reduces the instant values of $\Delta T$ in FIG. 5A, results in bigger deviations of $\Delta T$ on the $T(\Delta T)$ of FIG. 5B, and $\Delta T(t)$ of FIG. 5C. FIGS. 5B and 5C also represent the effect of digital filtering of some recorded electromagnetic noise by applying the method of running average, where k7 represents a filtering coefficient of the number of consecutively averaged datapoints (in this case, 7). This significantly reduced the noise and made the heat effects of phase transformations more clearly determinable. The actual phase transformation temperatures on FIGS. 5B and 5C are determined by the sudden change of the rate at which ΔT decreases as a function of the temperature (T) or the time (t).

Figure 6B:
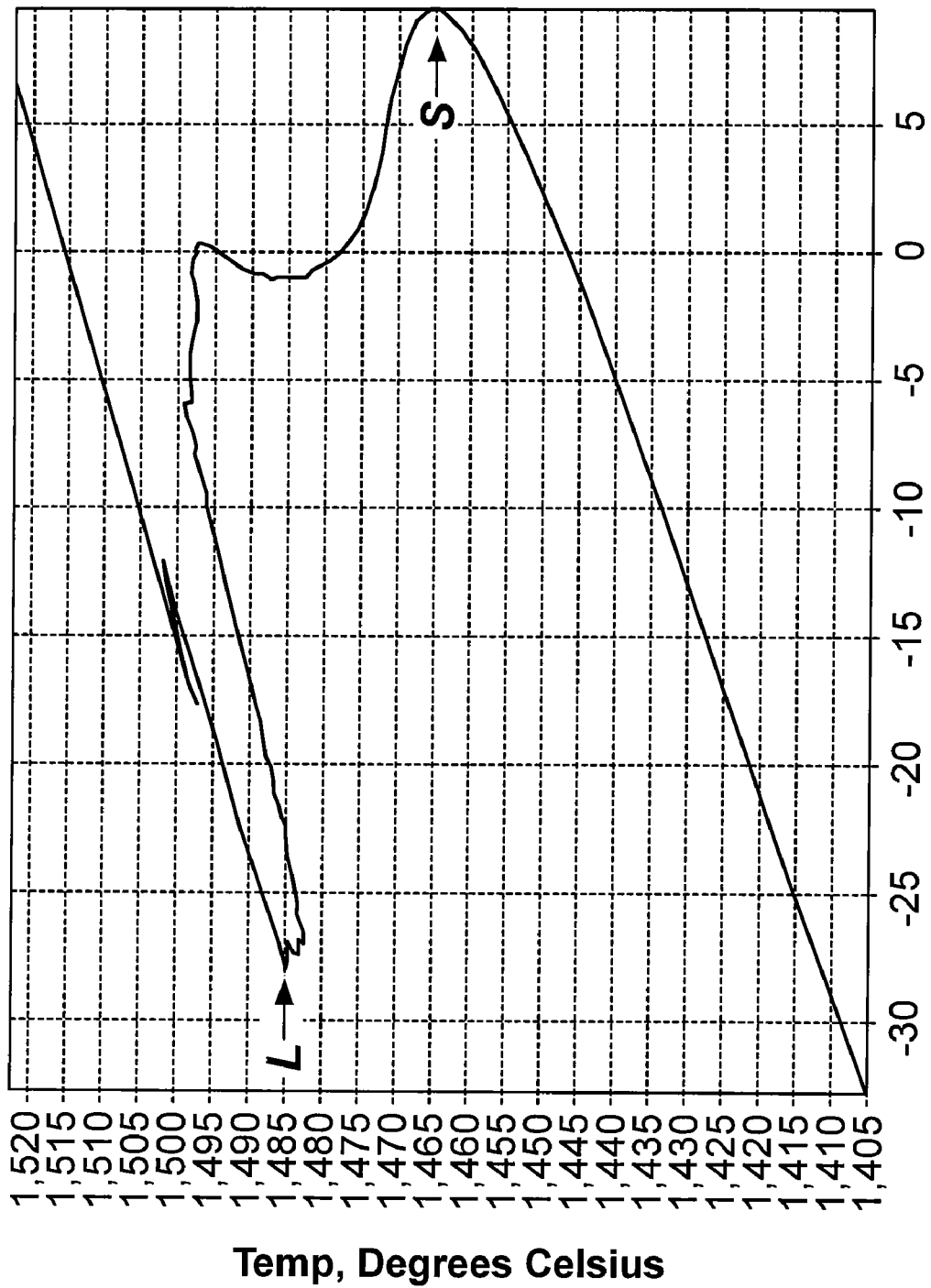
FIG. 6B illustrates the heat release during solidification of the specimen of FIG. 6A.
Figure 6C:
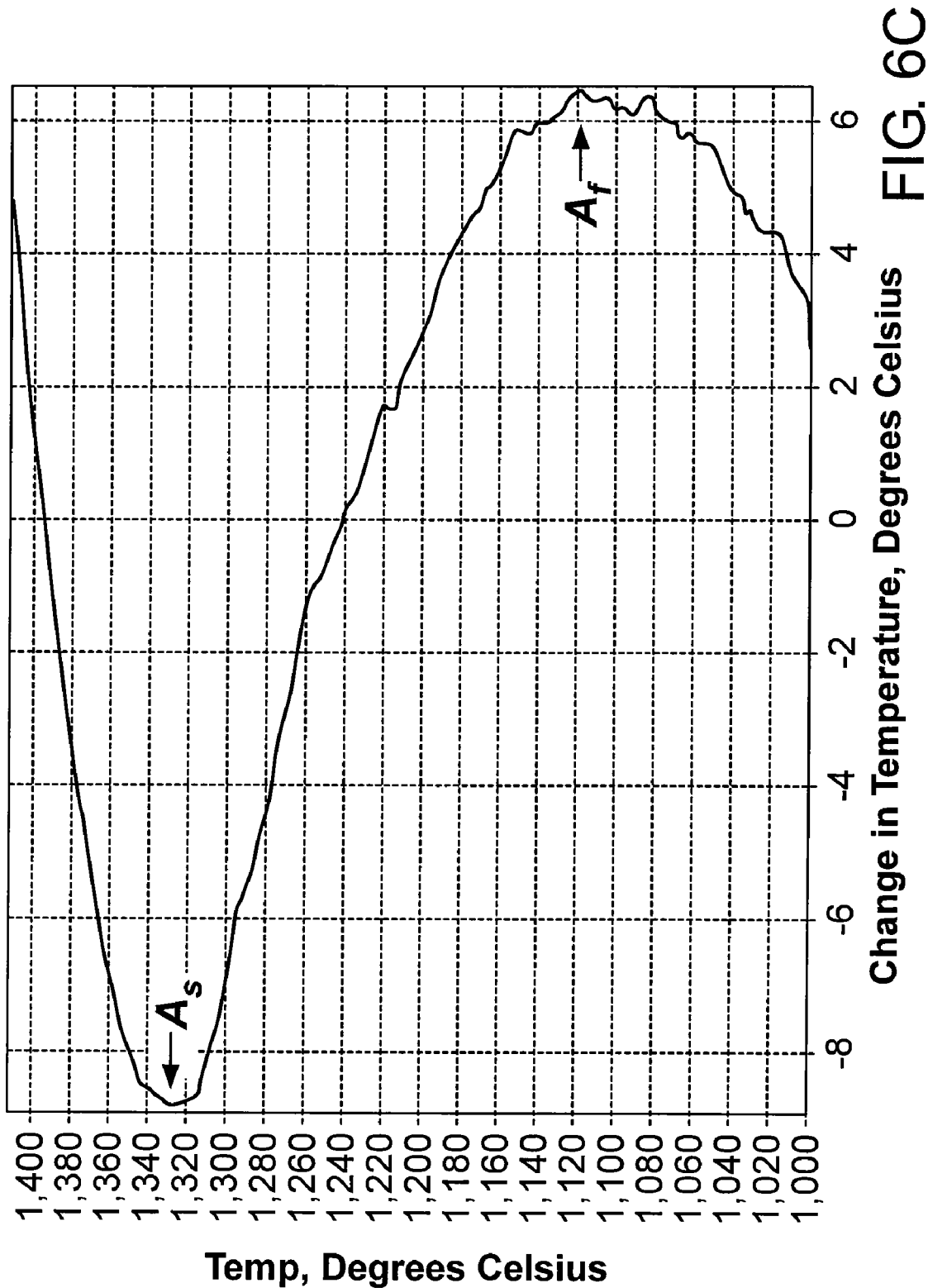
FIG. 6C illustrates the heat release during solid state transformation of delta ferrite to austenite of the specimen of FIG. 6A.
Figure 6D:
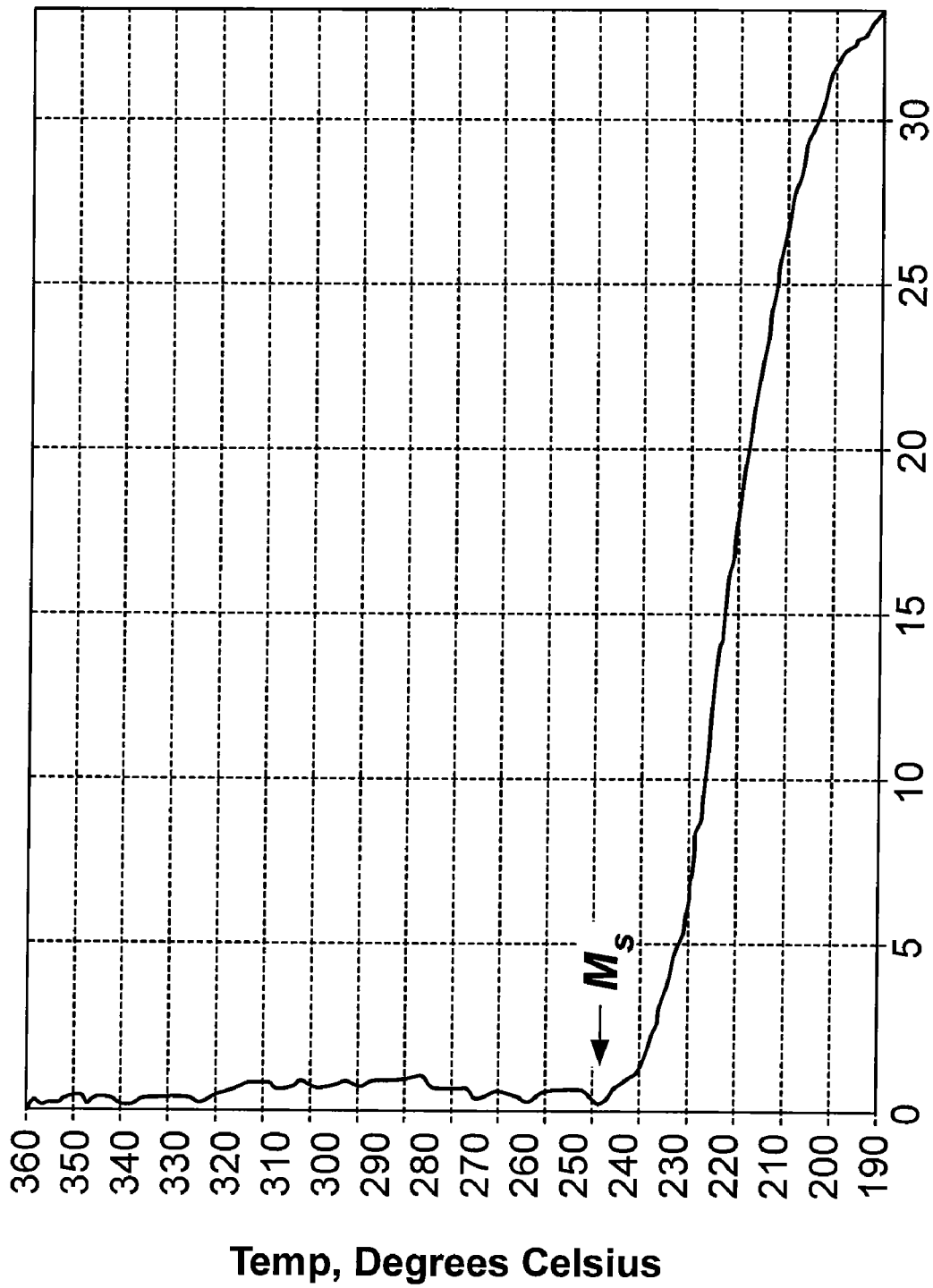
FIG. 6D illustrates the beginning of heat release during solid state transformation of austenite to martensite of the specimen of FIG. 6A.
Figure 6E:
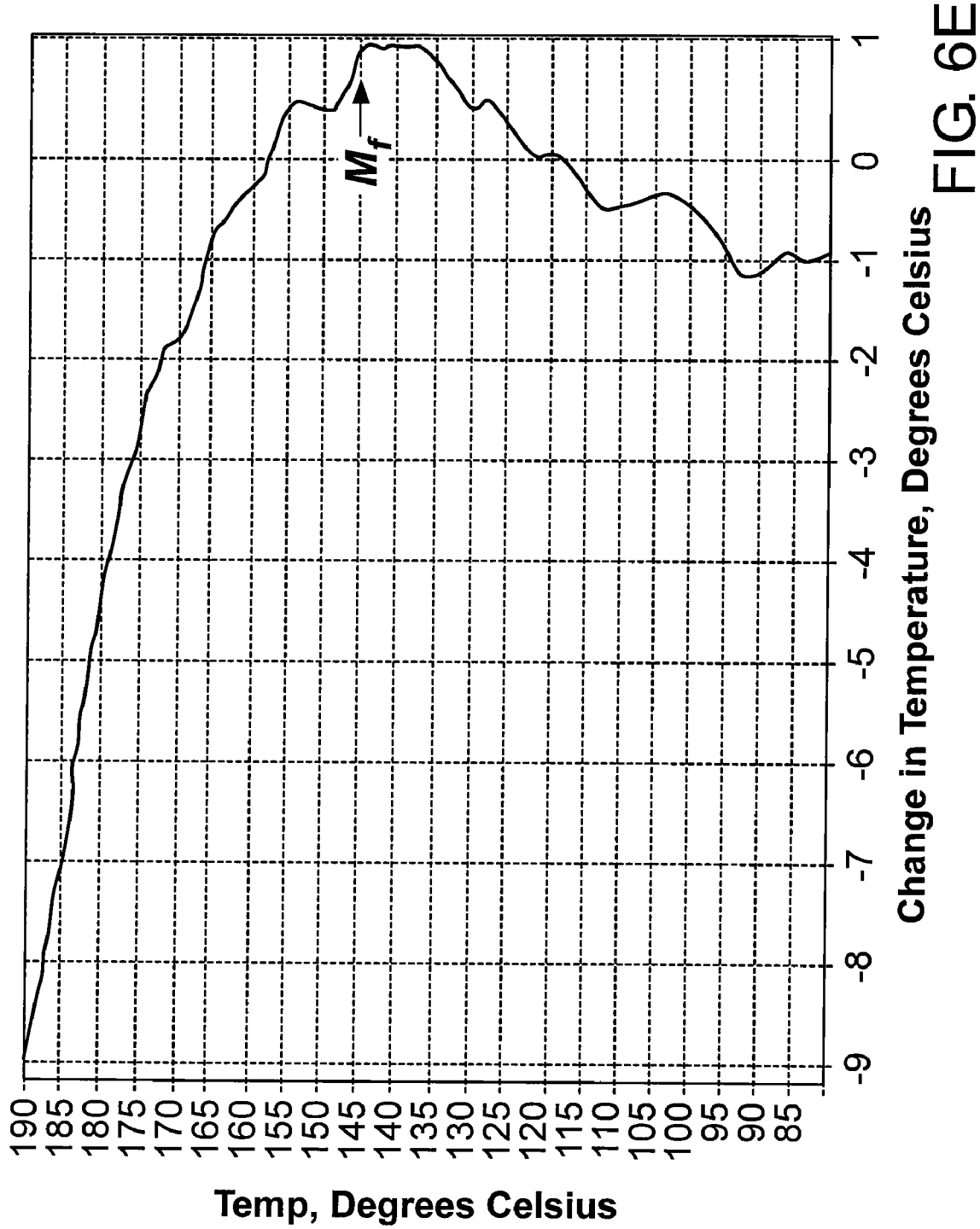
FIG. 6E illustrates the finishing of heat release during solid state transformation of austenite to martensite of the specimen of FIG. 6A.

Referring next to FIGS. 6A through 6E, a typical thermal history obtained with the device and method of the present invention is shown, where the thermal effects of phase transformations are revealed by the SSDTA software 40. In this case, the specimen was a stainless steel (12Cr-6.5Ni-2.5Mo), where the maximum temperature was 1539 degrees Celsius, and the cooling time between 800 degrees Celsius and 500 degrees Celsius ($\Delta t_{8/5}$) was 16.9 seconds. Referring first to FIG. 6A, two measured thermal histories are shown, with the temperature (in degrees Celsius) along the ordinate shown against the time (in seconds) along the abscissa. Referring next to FIG. 6B, the heat release during solidification as delta ferrite is shown. This is a result of the SSDTA software 40 processing the measured cooling history by generating a local reference curve. The determined liquidus and solidus temperatures are shown on this curve as points L and S. Referring next to FIG. 6C, the heat release during solid state transformation of delta ferrite to austenite is shown. As with FIG. 6B, this results from the processing by the SSDTA software 40 of the measured cooling history by SSDTA generating a local reference curve. The determined transformation starting and finishing temperatures on this curve are shown as points $A_S$ and $A_F$. Referring next to FIG. 6D, the beginning of heat release during solid state transformation of austenite to martensite is shown. As before, this is a result of processing the measured cooling history by generating a local reference curve. Because in this case the thermal effect is large, separate local references curves are used to determine the transformation starting and finishing temperatures. The determined transformation starting temperature on this curve is shown as $M_S$. Referring next to FIG. 6E, the finishing of heat release during solid state transformation of austenite to martensite is shown, which is also derived from processing the measured cooling history by generating a local reference curve. Because in this case the thermal effect is large, separate local references curves are used to determine the transformation starting and finishing temperatures. The determined transformation finishing temperature is shown as point $M_F$ on this curve.

Figure 7:
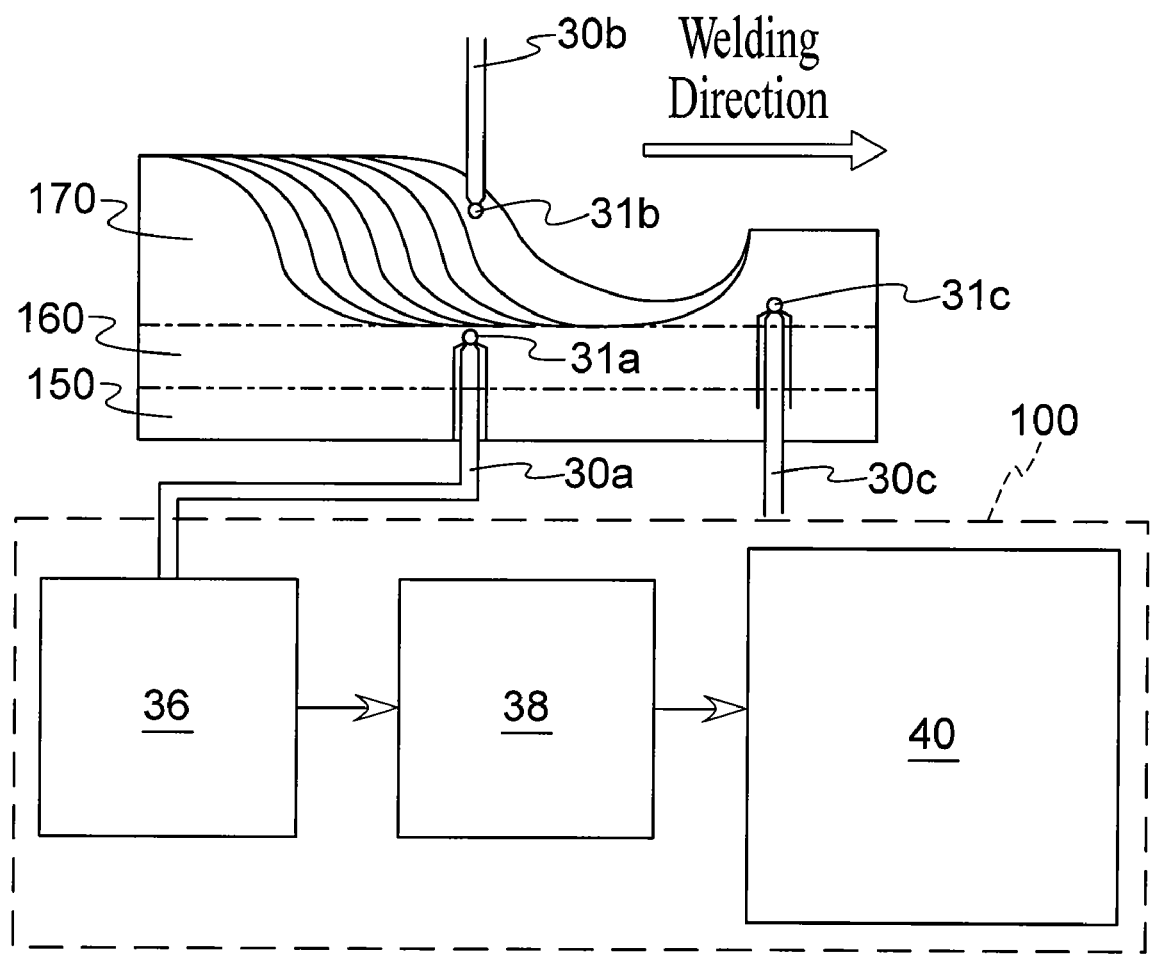
FIG. 7 illustrates the SSDTA method according to an aspect of the present invention being conducted on a fusion weld, showing three possible locations for a temperature measuring sensor, as well as data acquisition and calculation equipment.

Referring next to FIG. 7, an application of the SSDTA method to a fusion welding situation is shown. As with the device 10 of FIGS. 1 through 4, the temperature measurements are performed by thermocouples 30 that are capacitor discharge welded into holes formed in the base metal 150 so that the thermocouples tips 31 would coincide with the HAZ 160 or weld metal 170. Manual plunging of thermocouples 30 into the molten pool can also be conducted. The signal from thermocouple 30 is digitally acquired by digital acquisition system 36 and computation system 38 as a measured thermal history, which is then opened by SSDTA software 40. This software 40 calculates a preliminary reference thermal cycle by well known analytical formulae using the parameters of the measured thermal history, including initial (preheat) temperature ($T_0$), maximum temperature ($T_P$), and cooling time between eight hundred and five hundred degrees Celsius (Δt):

$$T = T_0 + \theta_k \left(\frac{\Delta t}{t}\right)^{\frac{1}{k}} \exp - \left[\frac{\theta_k^k \Delta t}{ket(T_P - T_0)^k}\right] \quad (1)$$

where:

$$\frac{1}{\theta_k^k} = \left(\frac{1}{(500 - T_0)^k} - \frac{1}{(800 - T_0)^k}\right). \quad (2)$$

In the above, θ is an expression used for simplification of the way the previous formula is presented, while k is related to heat extraction capacity of the processed object. The preliminary reference cycle is then subjected to optimization by the least square method or other methods, varying the above mentioned parameters and by shifting it along the temperature and time axis. In this particular case, the optimization is done for the cooling part of the thermal history and generates a constantly decreasing function ΔT(t) with a predetermined rate, typically three to five degrees Celsius per each one hundred degree Celsius cooling increment. The obtained solution is presented as two diagrams: $T_M(\Delta T)$, as shown in FIG. 5B, and ΔT(t), as shown in FIG. 5C. The SSDTA software 40 allows further optimization of the solution by manually changing the parameters of the calculated reference cycle. FIG. 5A presents an example of optimization of the calculated thermal history. In this case, the position of $T_R(t)$ towards $T_M(t)$ is optimized by changing $\Delta t_{8/5}$; increasing $\Delta t_{8/5}$ shifts $T_R(t)$ closer to $T_M(t)$ thus reducing ΔT(t) and increasing sensitivity to the thermal effects of bainitic and martensitic transformations, as shown in FIGS. 5B and 5C.

Referring next to FIG. 8, again in situations where the temperature measuring sensors 30 are thermocouples, an approach for grounding the thermocouples is used to sense and process temperature signals. In a typical temperature-measuring approach, thermocouples generate a low level voltage signal that can be interfered with by strong electromagnetic fields generated by external devices, such as electric power sources or electric power lines. Approaches are needed to reduce the electromagnetic noise in thermocouples and related sensors.

Conventional approaches to reducing the electromagnetic noise in thermocouples and related sensors employ twisted and shielded extension wires, and in the case of a metal sheathed thermocouple, grounding a measuring instrument (typically, a data acquisition system) to the thermocouple sheath through the extension wire shield. In one form, the direct grounding of the measuring instrument is through a connection at a random location on the specimen. In situations involving the passage of electric current through the specimen (for example, during a typical metal processing application), the relative locations of the thermocouple, the measurement ground, the power application, and the power source ground may affect the accuracy of thermocouple measurements. In situations involving a liquid metal in a mold made of electric insulating material (such as ceramic), such a grounding approach would be inapplicable, as the data acquisition system should be grounded to the metal (in this case, molten metal), which the thermocouple is in contact with, and as close to the thermocouple as possible. In situations involving liquid metal in a mold made of electric conductive material (such as metal), such an approach (grounding to the mold, for example) would be ineffective because of the unstable electrical contact between the mold and the metal, which results from surface oxidation and shrinkage of the molten metal during its solidification and solid state cooling.

Figure 8:
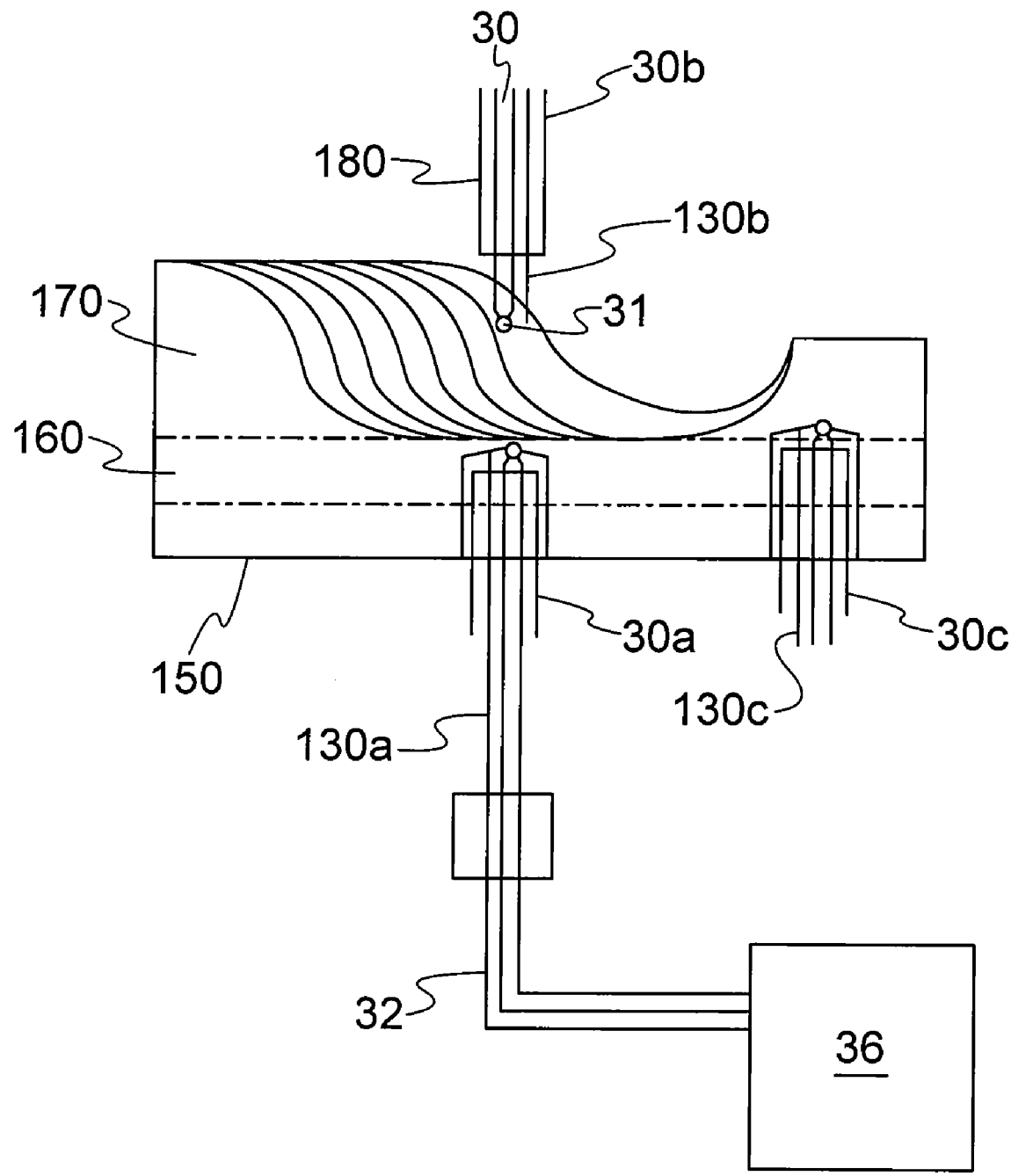
FIG. 8 illustrates the SSDTA method of FIG. 7, further including grounding means.

In the SSDTA method of the present invention, the thermocouples 30 are exposed, which places them in direct contact with the specimen 18 under investigation. Such contact provides a direct electrical path, thereby making the conventional grounding approaches incompatible with the present invention. In the embodiment shown, there are three temperature sensing devices (in the form of thermocouples 30A, 30B and 30C). Each work independently of the others, and may be used singly or in any combination to effect the desired temperature measuring. In the present invention, the thermocouples 30 generate a low level signal in the range between −8 millivolts and +80 millivolts. The interference discussed above can compromise the accuracy of thermocouple 30 temperature measurement and, in the most severe cases, make such measurement impossible. The SSDTA method of the present invention is based on the evaluation of local thermal effects available in the overall thermal history of a material specimen subjected to thermal or thermo-mechanical processing. Thus, a significant reduction or complete elimination of the electromagnetic noise in thermocouple measurements is helpful in establishing reliable and accurate application of the SSDTA method where thermocouples 30 are used as the temperature measuring sensors. The grounding approach shown in FIG. 8 is useful in-situations involving direct contact of the thermocouple 30 with the specimen 18 Grounding the measuring instrument (i.e., the data acquisition system 36) to the specimen 18 in a position close to the thermocouple 30 makes the data acquisition system 36 more insensitive to the electromagnetic noise generated in the processed metallic specimen and to the changing electric paths in it. The data acquisition system 36 is grounded to the specimen (shown as a weld metal 170) through a grounding wire 130 that is made of the same type of wire as that of the thermocouple 30 and is grounded in a close location to the thermocouple tip 31. The grounding wire 130 is connected to the data acquisition system 36 through an extension wire shield 32. Thus, the thermocouple 30 is in contact with the specimen 18 so that it can measure the specimen 18 temperature, while the data acquisition system 36 (i.e., the measuring instrument) is grounded to the specimen 18 close to the thermocouple 30. In situations calling for measuring the temperature of a solid metal specimen 18, both the ground wire 130 and the thermocouple tip 31 are capacitor discharge welded to the specimen 18 with a spacing of approximately 1 mm between them, as shown in the figure.

In situations involving the measurement of liquid metal temperature (i.e., that corresponding to the melted state or welding pool of weld metal 170), both the thermocouple 30B and the ground wire 130 are held by a ceramic insulator 180 at a spacing of approximately 1 millimeter between them. The thermocouple 30B and the ground wire 130 are brought into simultaneous contact with the metal by inserting their tips into liquid metal 170 (as shown in the figure), or by pouring liquid metal over them.

The temperature in a particular area of interest in a specimen 18 subjected to processing by fusion or solid state welding, casting, heat treatment, or other thermal or thermo-mechanical application is measured by a single contact or non-contact temperature sensor 30. The signal of the temperature sensor, which is typically analog, is conditioned (usually amplified and sometimes filtered), converted into digital form, then converted to a corresponding temperature signal and recorded into the operating memory of a computation system 38, where a predetermined sampling rate can be used. The signal processing can be performed by either a custom-designed or commercially available data acquisition system 36. Likewise, an algorithm (as discussed below in conjunction with FIG. 9) can be utilized, and may be in a form known to those skilled in the art, such as software that can be loaded into memory of computation system 38.

The measured thermal history carries information about the heat effects associated with the phase transformations of specimen 18. The solid-solid and solid-liquid phase transformations and structural changes that occur during heating consume or release heat, which results in changes of the heating rate inside the temperature range of the particular transformation. Similarly, the phase transformations and structural changes during cooling release or consume heat, which results in changes of the cooling rate in the respective temperature ranges of transformation. In the conditions of steep thermal gradients and high heating and cooling rates, which are typical for most of the material processing technologies, these thermal effects are quite small and barely discernible over the recorded thermal history. The device 10 and accompanying SSDTA method are configured to reveal this data, which utilizes only one recorded thermal history, in comparison to traditional DTA (which utilizes two thermocouples measuring the thermal history of a reference specimen with no phase transformations). The approach of the traditional method is replaced in the present invention by a calculated reference thermal cycle derived from analytical formulae or numerical modeling, an example of which follows.

The temperature difference $\Delta T(t)$ between the measured thermal history ($T_M(t)$) and the calculated reference thermal cycle ($T_R(t)$) is plotted as function of the time according to the following equation:

$$\Delta T(t) = T_M(t) - T_R(t) \quad (1)$$

Then based on $T_M(t)$ and $\Delta T(t)$ the dependence $T_M(\Delta T)$ is plotted. The thermal effects of the phase transformations, which are present with the measured thermal history, cause local changes of $\Delta T$ over the $T_M(\Delta T)$ and $\Delta T(t)$ curves, whose beginnings and ends coincide with the starting and finishing temperatures of the phase transformations, as shown in FIGS. 5A through 5C.

The sensitivity to the thermal effects of phase transformations, and respectively the accuracy in determining the transformation start and finish temperatures, strongly depend on the ratio between the current value of $\Delta T$ and the magnitude of its change due to the thermal effect of transformation, FIGS. 5A through 5C. Revealing smaller thermal effects requires smaller temperature differences between $T_M(t)$ and $T_R(t)$. The phase transformations and structural changes during heating and cooling cause local increasing or decreasing in $\Delta T(t)$. Consequently, slightly increasing the general trend of $\Delta T(t)$ in the case of its local decreasing and slightly decreasing general trend $\Delta T(t)$ in the case of its local increasing will facilitate sharper detection of the transformation starting and finishing temperatures.

The device 10 and SSDTA method achieves optimal sensitivity to the heat effect of a particular phase transformation. This is done by optimizing the calculated reference thermal cycle towards the recorded thermal history in order to obtain predetermined values and trend of change in $\Delta T(t)$ in a particular temperature range.

Figure 9:
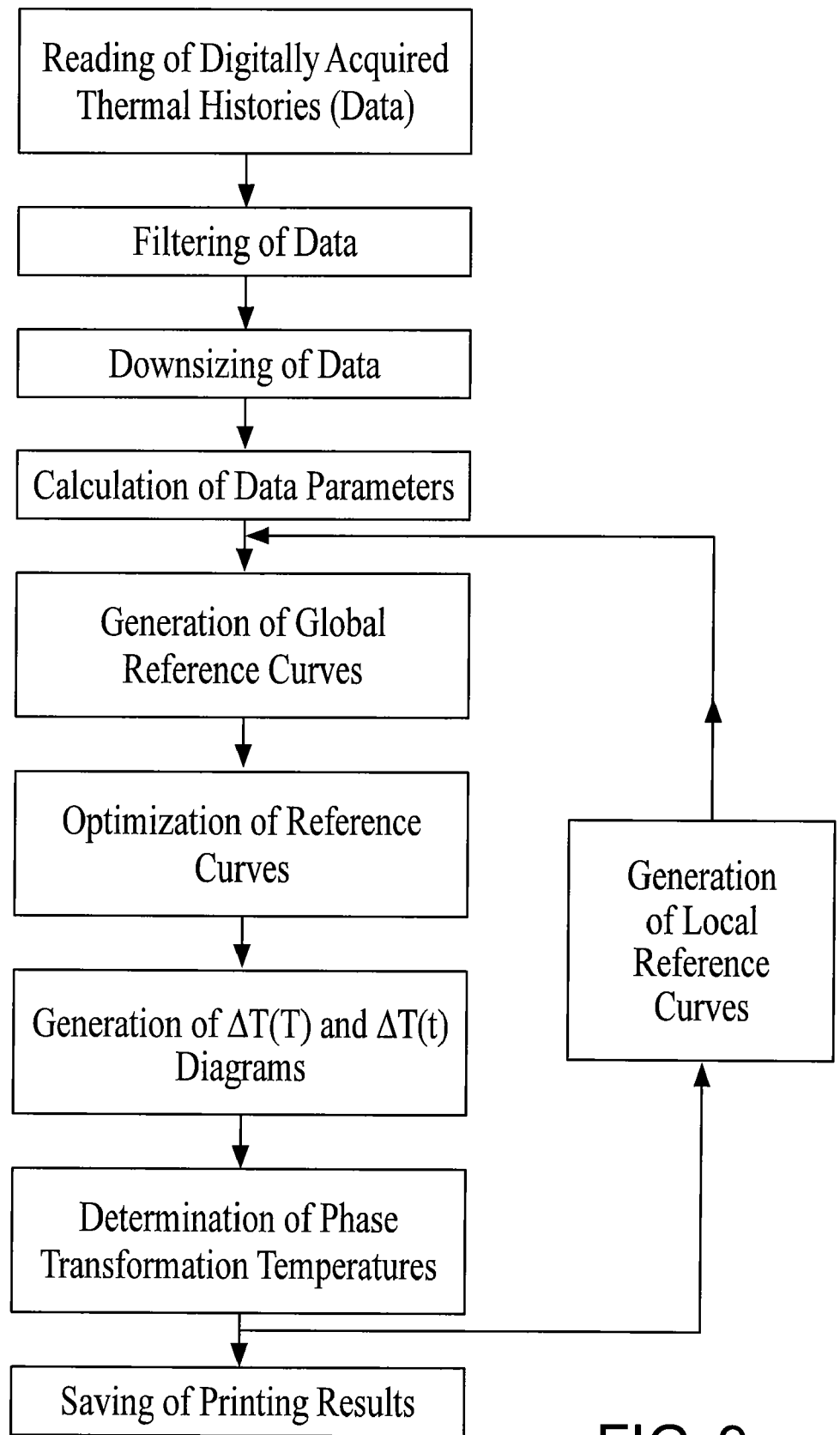
FIG. 9 illustrates a flow chart associated with a single sensor differential thermal analysis algorithm according to the present invention.

Referring next to FIG. 9, a flow chart depicting how an algorithm for conducting the SSDTA of the present invention is shown. The first step includes browsing folders and selecting one or several files acquired by the data acquisition system 36, then reading and loading simultaneously the selected files. In the next step, the data is filtered. This includes detecting recorded high or low frequency noise, filtering of the recorded noise by running average, available digital filters or other filtering procedures, then saving the filtered data (such as to memory). In a next step, the data is downsized. This includes averaging the recorded temperature data to a predetermined number of data points per incremental temperature (such as degrees Celsius), then generating and saving the new (downsized) data with a predetermined number of data points per the temperature increment. In a next step, data parameters are calculated. This includes determining the initial and maximal temperatures ($T_0$ and $T_{MAX}$), then calculating heating and cooling rates and heating and cooling times in selected temperature ranges, then calculating dwell times above selected temperatures, in addition to determination of inflection points, and then saving these parameters in the files of the filtered or downsized data. In a next step, global reference curves are generated separately for both the entire heating part and the entire cooling part of the data.

The reference curves may be generated by available analytical formula, by available procedures for generation of fitting curves, or by numerical modeling of heat transfer in the particular conditions of thermal/thermo-mechanical processing or simulation of processing. In another step, the reference curves are optimized. This includes establishing optimization criteria for best fit with the data, optimizing the parameters of the reference curves by available optimization procedures (examples of which may include the least square method, the "steepest slope" method, the Levenberg-Marquardt method, or the like). In this optimization, the data inflection points can be used as reference points. In the next step, $\Delta T(T)$ and $\Delta T(t)$ diagrams can be generated, where the functions $\Delta T(T)$ and $\Delta T(t)$ are calculated using $\Delta T = T_M - T_R$ ($T_M$ is the measured temperature at each data point and $T_R$ is the corresponding temperature of the optimized reference curve). These generated diagrams can then be saved in a single file together with the parameters of optimization. After that, phase transformation temperatures can be determined. This can be by manual determination of the phase transformations starting and finishing points, followed by automatic determination of the temperatures and time at these points. The criteria and procedure for fully automatic determining of the phase transformations temperatures can also be applied, after which these diagrams can be saved and printed or pasted in other files. In a next step, local reference curves can be generated in a manner generally similar to that of the step involving generation of global reference curves. In addition, this allows generation of local reference curves for each temperature range where phase transformations are expected to occur, as well as where phase transformations are detected in accordance with the previous step. Then, the generation of $\Delta T(T)$ and $\Delta T(t)$ diagrams and the determination of the phase transformation temperatures of the previous two steps can be repeated. In the next step, the results can be saved and printed. First, save all final solutions in separate file folders containing optimized parameters of the reference curves, $\Delta T(T)$ and $\Delta T(t)$ diagrams as well as phase transformation temperatures. After that, the results can be printed as a separate report or pasted into a word processing document.

Having described the invention in detail and by reference to preferred embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

We claim:

1. A method of conducting single sensor differential thermal analysis of a material selected from the group consisting of metals and metal alloys, said method comprising:
    placing a specimen of said material in thermal communication with a heat source;
    heating said specimen with said heat source;
    acquiring temperature data associated with said specimen using a single sensor;
    calculating reference data based on said acquired temperature data;
    computing temperature differences based on comparison between said acquired temperature data and said calculated reference data;
    generating phase transformation temperatures based on said computed temperature differences; and
    outputting said generated phase transformation temperatures to a user-compatible medium.

2. The method of claim 1, wherein said conducting single sensor differential thermal analysis is performed in conjunction with a metal processing application, selected from the thermal or thermo-mechanical processing group consisting of welding, surfacing, hardfacing, brazing, soldering, thermal cutting, casting, heat treatment, forging, rolling, extruding and surface melting.

3. The method of claim 1, wherein said conducting single sensor differential thermal analysis comprises simulating non-equilibrium solid-liquid and solid-state phase transformations and structural changes of said specimen.

4. The method of claim 1, wherein said acquiring temperature data further comprises reducing electromagnetic noise exposure of a data acquisition system that is signally coupled to said single sensor.

5. The method of claim 4, wherein said reducing electromagnetic noise exposure comprises grounding said data acquisition system and said single sensor.

6. The method of claim 1, wherein said calculated reference data is generated by a formula according to the following equation:

$$T = T_0 + \theta_k \left(\frac{\Delta t}{t}\right)^{\frac{1}{k}} \exp - \left[\frac{\theta_k^k \Delta t}{ket(T_P - T_0)^k}\right],$$

$$\text{where } \frac{1}{\theta_k^k} = \left(\frac{1}{(500 - T_0)^k} - \frac{1}{(800 - T_0)^k}\right)$$

and T represents said calculated reference data as a thermal cycle, $T_o$ represents initial (preheat) temperature, $T_p$ represents maximum temperature, e represents the natural logarithm base, $\Delta_t$ represents cooling time between eight hundred and five hundred degrees Celsius and k is related to a heat extraction capacity of said specimen.

7. The method of claim 3, wherein said simulating, further comprises:
    operating a feedback-based control loop;
    controlling a simulation device through a feedback-based control so that said simulation device responsively follows a predetermined thermal history that is formed from said computed temperature difference;
    acquiring power output history data associated with said controlling said simulation device;
    filtering said acquired power output history data;
    applying said filtered power output history data to a new specimen;
    acquiring a thermal history of said new specimen;

saving said acquired thermal history of said new specimen; and processing said acquired thermal history of said new specimen with said single sensor differential thermal analysis.

8. The method of claim 7, further comprising compensating heating and cooling rates in response to thermal effects produced during at least one of phase transformation and structural changes in said specimen.

9. The method of claim 1, wherein said outputting said generated phase transformation temperatures to a user-compatible medium comprises placing said generated phase transformation temperatures on an electronic display.

10. The method of claim 1, wherein said outputting said generated phase transformation temperatures to a user-compatible medium comprises placing said generated phase transformation temperatures on a computer-compatible memory device.

11. The method of claim 1, wherein said outputting said generated phase transformation temperatures to a user-compatible medium comprises printing said generated phase transformation temperatures.

* * * * *